(12) United States Patent
deKemp et al.

(10) Patent No.: US 7,813,841 B2
(45) Date of Patent: Oct. 12, 2010

(54) RUBIDIUM ELUTION SYSTEM CONTROL

(75) Inventors: Robert A. deKemp, Ottawa (CA); Ran Klein, Ottawa (CA)

(73) Assignee: Ottawa Heart Institute Research Corporation, Ottawa (CA)

( * ) Notice: Subject to any disclaimer, the term of this patent is extended or adjusted under 35 U.S.C. 154(b) by 446 days.

(21) Appl. No.: 11/372,149

(22) Filed: Mar. 10, 2006

(65) Prior Publication Data

US 2007/0213848 A1    Sep. 13, 2007

(51) Int. Cl.
G05D 7/00    (2006.01)
G05D 11/00   (2006.01)

(52) U.S. Cl. ..................... 700/282; 700/31
(58) Field of Classification Search ........... 700/282, 700/283, 285, 31
See application file for complete search history.

(56) References Cited

U.S. PATENT DOCUMENTS

| | | | |
|---|---|---|---|
| 4,585,009 A * | 4/1986 | Barker et al. | 600/432 |
| 4,585,941 A * | 4/1986 | Bergner | 250/363.02 |
| 4,975,583 A | 12/1990 | Spowart | |
| 6,049,026 A * | 4/2000 | Muschler | 424/93.7 |
| 6,641,783 B1 * | 11/2003 | Pidgeon et al. | 422/70 |
| 6,713,765 B2 | 3/2004 | Testardi | |
| 6,731,971 B2 * | 5/2004 | Evans et al. | 600/431 |
| 6,733,477 B2 * | 5/2004 | Cowan et al. | 604/181 |
| 6,733,478 B2 * | 5/2004 | Reilly et al. | 604/189 |
| 6,901,283 B2 * | 5/2005 | Evans et al. | 600/431 |
| 6,928,338 B1 * | 8/2005 | Buchser et al. | 700/265 |
| 7,169,135 B2 * | 1/2007 | Duchon et al. | 604/246 |
| 7,174,240 B2 * | 2/2007 | Shturman et al. | 700/282 |

FOREIGN PATENT DOCUMENTS

| | | |
|---|---|---|
| JP | 7231884 A | 9/1995 |
| JP | 2000131443 A | 5/2000 |

OTHER PUBLICATIONS

R. Klein. "Precise Control of Eluted Activity from a Sr/Rb Generator for Cardiac Positron Emission Tomography" Thesis, University of Ottawa (Feb. 2005): 1-60. (partial document).*

R. Klein, et al. "Precision Control of Eluted Activity from a Sr/Rb Generator for Cardiac Positron Emission Tomography", Proceedings of the 26th Annual International Conference of the IEEE EMBS San Francisco, CA, USA, Sep. 1-5, 2004, pp. 1393-1396.

(Continued)

Primary Examiner—Ryan A Jarrett
(74) Attorney, Agent, or Firm—McCarthy Tétrault LLP

(57) ABSTRACT

A method of controlling an $^{82}$Sr/$^{82}$Rb elution system having a generator valve for proportioning a flow of saline solution between an $^{82}$Sr/$^{82}$Rb generator and a bypass line coupled to an outlet of the generator such that saline solution traversing the bypass line will merge with eluted saline solution emerging from the generator to provide an active saline solution. During each elution run, a plurality of successive concentration parameter values are obtained at predetermined intervals. Each concentration parameter value is indicative of a respective instantaneous activity concentration of the active saline solution. Respective error values between each concentration parameter value and a target activity concentration value of the elution run are computed. Error data based on a plurality of the computed error values is accumulated. Between successive elution runs, at least one performance parameter of the elution system is adjusted based on the accumulated error data.

17 Claims, 7 Drawing Sheets

OTHER PUBLICATIONS

Neil J. Epstein, et al. "A 82Rb Infusion System for Quantitative Perfusion Imaging With 3D PET", Applied Radiation and Isotopes 60, (2004) pp. 921-927.

Alvarez-Diaz, Teresa M. et al., Manufacture of Strontium-82/rubidium-82 generators and quality control of rubidium-82 chloride for myocardial perfusion imaging in patients using positron emission tomography, Applied Radiation and Isotopes, vol. 50, No. 6, 1999, pp. 1015-1023.

Yano, Y, et al., A Precision Flow-Controlled Rb-82 Generator for Bolus or Constant-Infusion Studies of the Heart and Brain, The Journal of Nuclear Medicine, vol. 22, No. 11, 1981, pp. 1006-1010.

Yano, Y, Essentials of a Rubidium-82 Generator for Nuclear Machine, International journal of radiation applications and instrumentation. Part A, Applied radiation and isotopes, vol. 38, No. 3, Great Britain, 1987, pp. 205-211.

Kensett, M.J. et al., Experience with a 82Sr/Rb Generator for Clinical Use, International journal of radiation applications and instrumentation. Part A, Applied radiation and isotopes, vol. 38, No. 3, Great Britain, 1987, pp. 227-231.

Saha, G. et al., Use of the 82Sr/82Rb Generator in Clinical PET Studies, International journal of radiation applications and instrumentation. Part B, Nuclear medicine and biology, vol. 17, No. 8, Great Britain, 1990, pp. 763-768.

Klein, Ran et al. "Precision Control of Eluted Activity from a Sr/Rb . . . Emission Tomography" Conference poster; 26th Annual International Conference of the IEEE EMBS (2004).

Klein, Ran "Precise 82RB Infusion System for Cardiac Perfusion Measurement Using 3D Positron Emission Tomography" (Submitted Feb. 2005).

Klein, Ran et al., "Precision-controlled elution of a 82Sr/82Rb generator for cardiac perfusion Imaging with positron emission tomography", Phys. Med.Biol. 52 (2007) 659-673.

* cited by examiner

RUBIDIUM ELUTION SYSTEM CONTROL

CROSS-REFERENCE TO RELATED APPLICATIONS

This is the first application filed for the present invention.

MICROFICHE APPENDIX

Not Applicable.

TECHNICAL FIELD

The present application relates in general to nuclear medicine and, in particular, to a rubidium elution control system.

BACKGROUND OF THE INVENTION

As is well known in the art, Rubidium ($^{82}$Rb) is used as a positron emission tomography (PET) tracer for non-invasive measurement of myocardial perfusion (blood flow).

Recent improvements in PET technology have introduced 3-dimensional positron emission tomography (3D PET). Although 3D PET technology may permit more efficient diagnosis and prognosis in patients with suspected coronary artery disease, the sensitivity of 3D PET requires very accurate control of the delivery of $^{82}$Rb activity to a patient being assessed.

FIGS. 1 and 2 illustrate a conventional rubidium elution system used for myocardial perfusion imaging. As may be seen in FIG. 1, the elution system comprises a reservoir of sterile saline solution (e.g. 0.9% Sodium Chloride Injection), a pump, and a strontium-rubidium ($^{82}$Sr/$^{82}$Rb) generator. In operation, the pump causes the saline solution to flow from the reservoir 4 and through the generator 8 to elute the $^{82}$Rb. The active solution output from the generator 8 is then supplied to a patient (not shown) via a patient outlet 10.

When the system 2 is not in use, the amount of $^{82}$Rb within the generator 8 accumulates until a balance is reached between the rate of $^{82}$Rb production (that is, $^{82}$Sr decay) and the rate of $^{82}$Rb decay. As a result, the $^{82}$Rb activity level in the active saline emerging from the generator 8 tends to follow a "bolus" profile 12 shown by the solid line in FIG. 2a. In particular, at the start of an $^{82}$Rb elution "run", the activity level rises rapidly and peaks, as accumulated $^{82}$Rb is flushed out of the generator 8. Thereafter, the activity level drops back to a substantially constant value. The maximum activity level $A_{max}$ (bolus peak) obtained during the run is dependent on the amount of accumulated $^{82}$Rb in the generator 8, and thus is generally a function of the system's recent usage history, principally: the current $^{82}$Rb production rate; the amount of accumulated $^{82}$Rb (if any) remaining at the end of the previous elution run; and the idle time since the previous run. The generally constant level of the bolus tail is dependent on the rate of $^{82}$Rb production and the saline flow rate produced by the pump 6.

As is well known in the art, $^{82}$Rb is generated by radioactive decay of the $^{82}$Sr, and thus the rate of $^{82}$Rb production at any particular time is a function of the mass of remaining $^{82}$Sr. As will be appreciated, this value will diminish (exponentially) through the useful life of the generator 8. The result is a family of bolus curves, illustrated by the dashed lines of FIG. 2a, mapping the change in elution system performance over the useful life of the generator 8.

Because of the high activity level of $^{82}$Rb possible in the generator 8, it is desirable to limit the total activity dosage delivered to the patient during any given elution run. The total elution time required to reach this maximum permissible dose (for any given flow rate) will therefore vary over the life of the $^{82}$Sr charge in the generator 8, as may be seen in FIG. 2b, where the total activity dose, represented by the area under each curve, is equal in both cases.

A limitation of this approach, particularly for 3D PET imaging, is that the delivery of a high activity rate over a short period of time tends to degrade image quality. Low activity rates supplied over a relatively extended period are preferred. As a result, the user is required to estimate the saline flow rate that will obtain the best possible image quality, given the age of the generator and its recent usage history, both of which will affect the bolus peak and tail levels. This estimate must be continuously adjusted throughout the life of the generator 8, as the $^{82}$Sr decays.

Accordingly, techniques for controlling an $^{82}$Rb elution system that enable a desired activity level to be supplied over a desired period of time, independently of a state of the $^{82}$Sr/$^{82}$Rb generator, remain highly desirable.

SUMMARY OF THE INVENTION

Accordingly, an object of the present invention is to provide techniques for controlling an $^{82}$Rb elution system.

The present invention therefore provides a method of controlling an $^{82}$Sr/$^{82}$Rb elution system having a generator valve for proportioning a flow of saline solution between an $^{82}$Sr/$^{82}$Rb generator and a bypass line coupled to an outlet of the generator such that saline solution traversing the bypass line will merge with eluted saline solution emerging from the generator to provide an active saline solution. During each elution run, a plurality of successive concentration parameter values are obtained at predetermined intervals. Each concentration parameter value is indicative of a respective instantaneous activity concentration of the active saline solution. Respective error values between each concentration parameter value and a target activity concentration value of the elution run are computed. Error data based on a plurality of the computed error values is accumulated. Between successive elution runs, at least one performance parameter of the elution system is adjusted based on the accumulated error data.

BRIEF DESCRIPTION OF THE DRAWINGS

Further features and advantages of the present invention will become apparent from the following detailed description, taken in combination with the appended drawings, in which.

DETAILED DESCRIPTION OF THE PREFERRED EMBODIMENT

The present invention provides a Rubidium ($^{82}$Rb) elution and control system in which the $^{82}$Rb activity rate delivered to a patient can be controlled substantially independently of the condition of the $^{82}$Sr/$^{82}$Rb generator. Representative embodiments are described below with reference to FIGS. 3-8.

Figure 3:
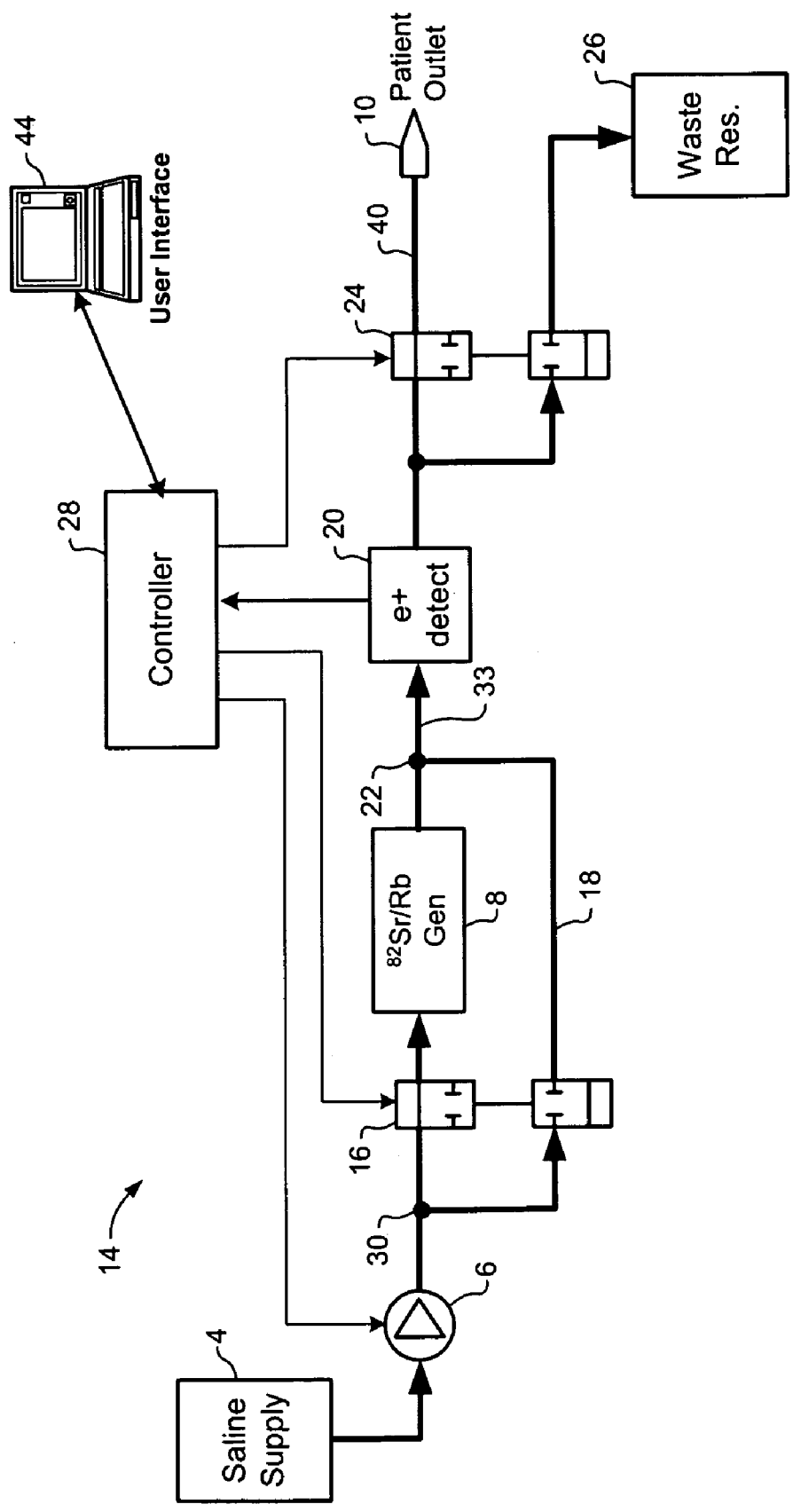
FIG. 3 is a block diagram schematically illustrating principal elements of a Rubidium elution system in accordance with an embodiment of the present invention.
Figure 4:
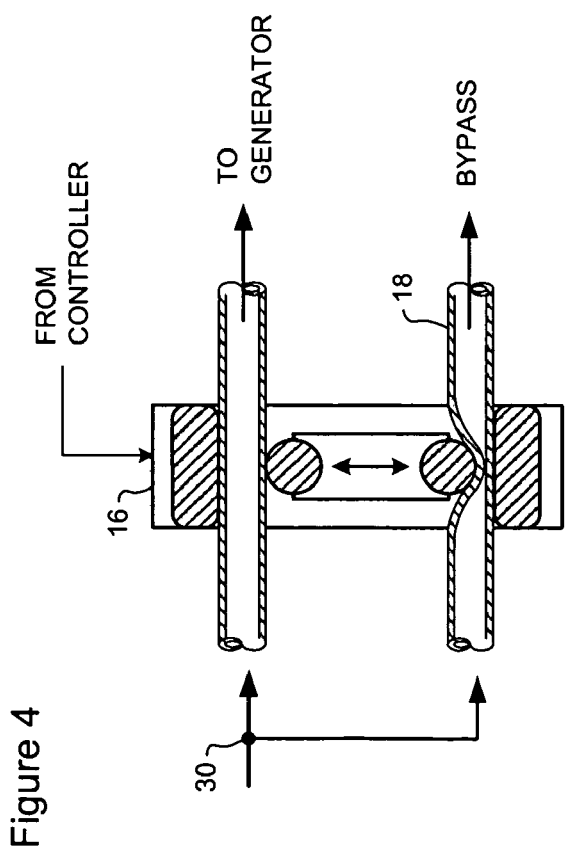
FIG. 4 illustrates a pinch-type valve arrangement usable in the elution system of FIG. 3.

In the embodiment of FIG. 3, the elution system comprises reservoir 4 of sterile saline solution (e.g. 0.9% Sodium Chloride Injection); a pump 6 for drawing saline from the reservoir 4 at a desired flow rate; a generator valve 16 for proportioning the saline flow between a strontium-rubidium ($^{82}$Sr/$^{82}$Rb) generator 8 and a bypass line 18 which circumvents the generator 8; a positron detector 20 located downstream of the merge point 22 at which the generator and bypass flows merge; and a patient valve 24 for controlling supply of active saline to a patient outlet 10 and a waste reservoir 26. A controller 28 is connected to the pump 6, positron detector 20 and valves 16 and 24 to control the elution system 14 in accordance with a desired control algorithm, as will be described in greater detail below.

If desired, the strontium-rubidium ($^{82}$Sr/$^{82}$Rb) generator 8 may be constructed in accordance with Applicant's co-pending U.S. patent application Ser. No. 11/312,368 entitled A Rubidium Generator For Cardiac Perfusion Imaging And Method Of Making And Maintaining Same, filed Dec. 21, 2005. In such cases, the pump 6 may be a low-pressure pump such as a peristaltic pump. However, other types of generator may be used. Similarly, other types of pump may be used, provided only that the pump selected is appropriate for medical applications and is capable of maintaining a desired saline flow rate through the generator.

The generator and patient valves 16, 24 may be constructed in a variety of ways. In principal, the generator valve may be provided as any suitable valve 16 arrangement capable of proportioning saline flow between the generator 8 and the bypass line 18. If desired, the generator valve may be integrated with the branch point 30 at which the saline flow is divided. Alternatively, the generator valve 16 may be positioned downstream of the branch point 30, as shown in FIG. 3. In embodiments in which flexible (e.g. Silicon) tubing is used to convey the saline flow, the generator valve 16 may be provided as one or more conventional "pinch" valves of the type illustrated in FIG. 4. The use of pinch valves is beneficial in that it enables saline flow to be controlled in a readily repeatable manner, and without direct contact between the saline solution and components of the valve. Factors associated with the design of the patient valve 24 are substantially the same as those discussed above for the generator valve 16, with the exception that the saline flow through the patient valve 24 is (or must be assumed to be) carrying radioactive $^{82}$Rb. Accordingly, while any suitable valve design may be selected for the patient valve 24, it is particularly beneficial to avoid direct contact between the active saline solution and valve components. For this reason, pinch valves are preferred for the patient valve 24.

Figure 5:
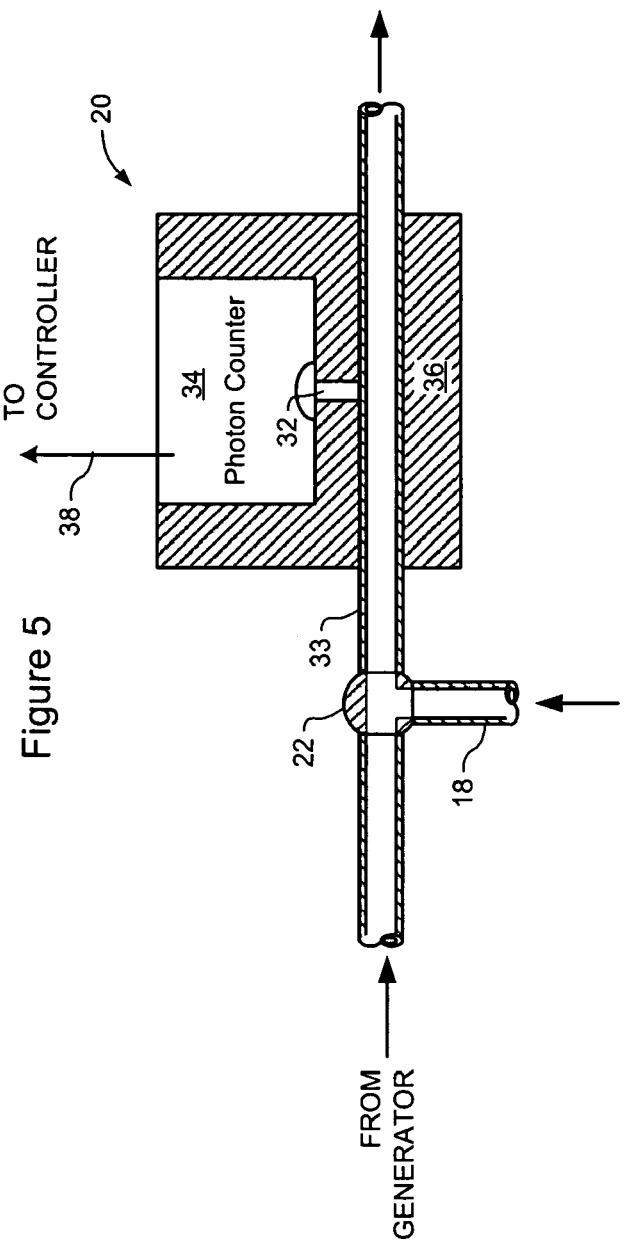
FIG. 5 schematically illustrates a positron detector usable in the elution system of FIG. 3.

As may be seen in FIG. 5, the positron detector 20 may conveniently be provided as a scintillator 32 disposed immediately adjacent to a feed-line 33 carrying the active saline solution; a photon counter 34 optically coupled to the scintillator 32; and a radiation shield 36 surrounding the scintillator 32 and photon counter 34. The scintillator 32 may be provided by a length of fluorescent optical fiber, which absorbs Beta (e+) radiation generated by $^{82}$Rb decay to produce a photon. The photon counter 34 (which may, for example be an H7155 detector manufactured by Hamamatsu) detects incident photons, and generates a detection signal 38 corresponding to each detected photon. The shielding 36, which may be constructed of lead (Pb), serves to shield the scintillator 32 and photon counter 34 from ambient Gamma and Beta radiation. In some embodiments, the radiation shield 36 is approximately ½ inch thick in the vicinity of the scintillation fiber 32, and may extend (in both directions) at least 5-times the feed-line 33 outer diameter from the scintillation fiber 32. This arrangement effectively suppresses ingress of ambient Gamma and Beta radiation along the channel through which the feed-line 33 passes. As a result, spurious photons are suppressed, and the rate at which photons are counted by the photon counter 34 will be proportional to the $^{82}$Rb activity concentration of the active saline solution adjacent to the scintillator 32. In the illustrated embodiments, the number of photons detected within a predetermined period of time is counted (e.g. by the controller 28), and the count value $C_{det}$ is used as an activity parameter which is proportional to the $^{82}$Rb activity concentration. If desired, a proportionality constant K between the activity parameter $C_{det}$ and the $^{82}$Rb activity concentration can be empirically determined.

In operation, the pump 6 and valves 16, 24 can be controlled to route saline solution through the system 14 in accordance with various modes of operation, as may be seen in FIGS. 6a-6d. Thus, for example, in a "Bypass-to-waste" mode of the system illustrated in FIG. 6a, the generator and patient valves 16, 24 are positioned to route the entire saline flow through the bypass line 18, and into the waste reservoir 26. This mode of operation is suitable for initializing the system 14 immediately prior to beginning an elution run.

Figure 6A:
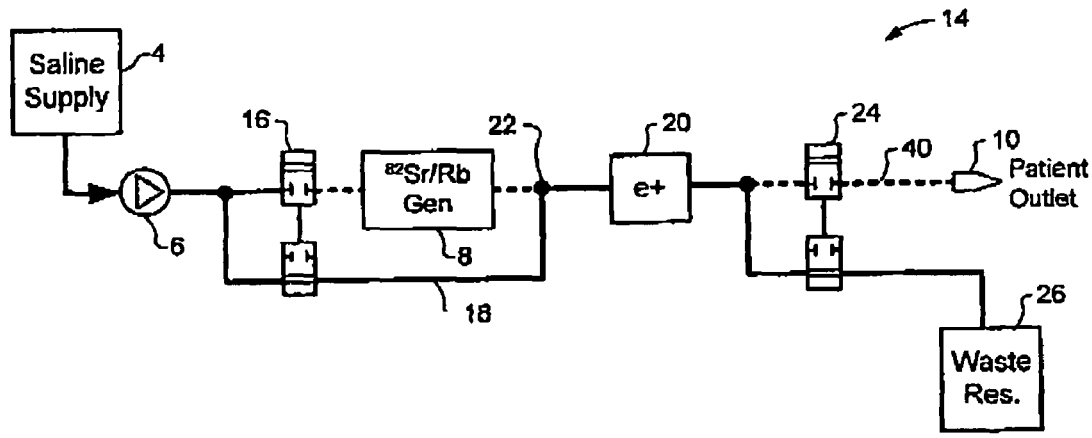
FIGS. 6a-6d schematically illustrate respective operating states of the Rubidium elution system of FIG. 3.
Figure 6B:
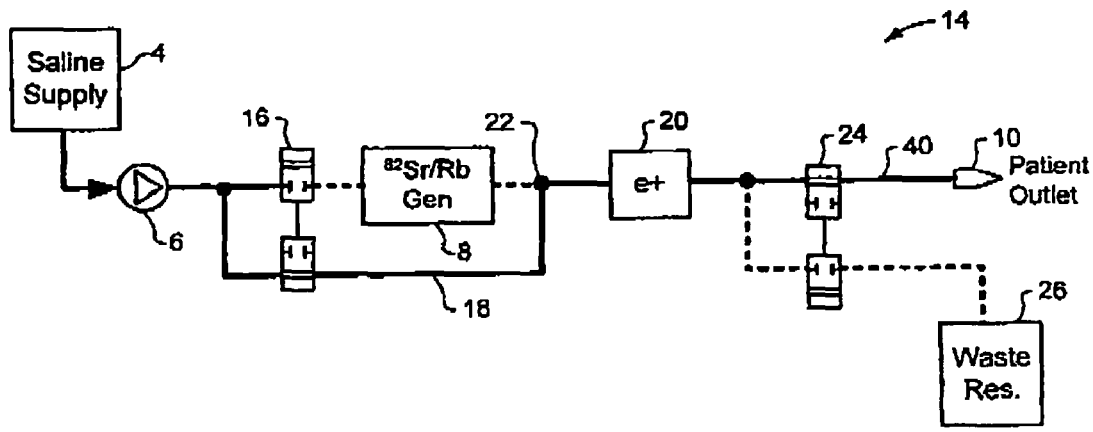

FIG. 6b illustrates a "patient line flush" mode of the system 14, in which the generator and patient valves 16, 24 are positioned to route the saline flow through the bypass line 18 and out through the patient outlet 10. This mode of operation may be used prior to an elution run to prime (that is, expel air from) the patient line 40 in preparation for insertion of the patient outlet into, for example, a vein of a patient. At the end of an elution run, this mode may also be used to flush any $^{82}$Rb activity remaining within the patient line 40 into the patient, thereby ensuring that the patient receives the entire activity dose required for the PET imaging.

Figure 6C:
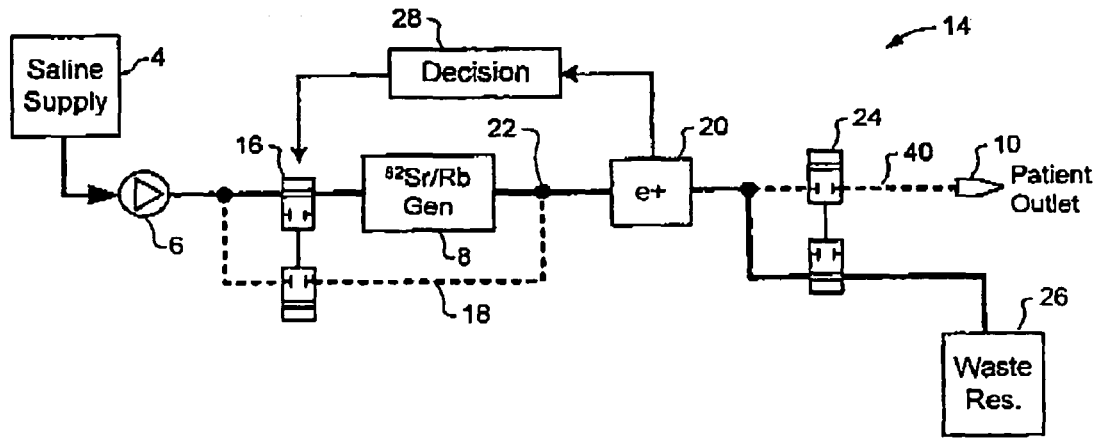

FIG. 6c illustrates a "waiting for threshold" mode of the system 14, in which the generator and patient valves 16, 24 are positioned to route the saline flow through the generator 8, and into the waste reservoir 26. This mode of operation is suitable during the beginning an elution run, while the $^{82}$Rb concentration is increasing from zero, but has not yet reached desired levels. Flushing this leading portion of the $^{82}$Rb bolus 12 to the waste reservoir 26 avoids exposing the patient to unnecessary $^{82}$Rb activity and allows the total activity dosage delivered to the patient to be closely controlled.

Figure 6D:
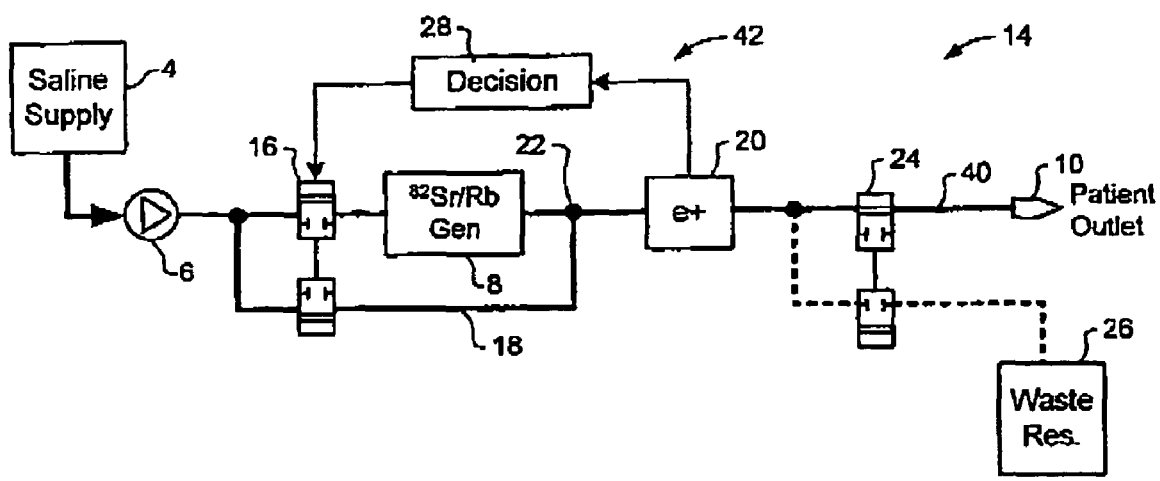

FIG. 6d illustrates an "elution" mode of the system 14, in which the generator valve 16 is actively controlled via a control loop 42 from the positron detector 20 to proportion saline flow through both the generator 8 and the bypass line 18. The generator 8 and bypass saline flows are then recombined (at 22) downstream of the generator 8 to produce an active saline solution having a desired $^{82}$Rb activity concentration. The patient valve 24 is positioned to direct the active saline solution to the patient outlet 10.

In the foregoing description, each operating mode is described in terms of the associated steps in performing an elution run to support PET imaging of a patient. However, it will be appreciated that this context is not essential. Thus, for example, one or more of the above operating modes may be used to facilitate calibration of the system, in which case the patient outlet 10 would be connected to a conventional dose calibrator (not shown), rather than a patient.

As will be appreciated from the foregoing discussion, each of the operating modes of the elution system is controlled by the controller unit 28 operating under software control. As a result, it is possible to implement a wide variety of automated processes, as required. Thus, for example, elution runs can be fully automated, based on user-entered target parameters, which allows the user to avoid unnecessary radiation exposure. Similarly, it is possible to automate desired system calibration and $^{82}$Sr break-through detection protocols, which ensures consistency as well as limiting radiation exposure of users. A further benefit of software-based elution system control is that data logs from each elution run can be easily maintained, which assists not only system diagnostics, but can also be used to ensure that the elution parameters (e.g. elution concentration and duration) specified for PET imaging have been satisfied.

As described above, in the "elution" mode of operation (FIG. 6d), the generator valve 16 is actively controlled via a control loop 42 from the positron detector 20 to proportion saline flow through both the generator 8 and the bypass line 18. Recombining the corresponding generator and bypass saline flows downstream of the generator 8 produces an active saline solution having a desired $^{82}$Rb activity concentration. Preferably, the control loop 42 is implemented using suitable software executing in the controller 28. Representative algorithms for implementing the control loop 42 are described below with reference to FIGS. 7 and 8.

In the embodiment of FIG. 7, the controller 28 implements a threshold-based control algorithm, in which the generator valve 16 is controlled by comparison of measured activity concentration to a desired activity concentration. If the measured concentration is higher than the desired concentration, the generator valve 16 directs saline flow to the bypass line 18 rather than the generator 8, and vice versa.

In general, the elution run is designed to generate a target $^{82}$Rb activity concentration which follows a desired function in time $C_M(t)$. In the embodiment of FIG. 7, $C_M(t)$ is a square-wave function having a predetermined constant activity concentration $C_M$ and duration ($t_2$-$t_1$), as may be seen by the dotted line of FIG. 7b. These parameters may be provided by explicit user input using the user interface 44 (FIG. 3), or calculated from other user-input parameters, such as a total activity dosage and saline flow rate. As will be appreciated, the target activity profile $C_M(t)$ need not be a square-wave function, other profiles may be used, such as a ramp function, if desired.

In some embodiments, the target activity profile $C_M(t)$ may define the desired $^{82}$Rb activity concentration at the patient outlet 10. In such cases, an adjusted target profile $C'_M(t)$ may be computed based on the selected flow rate and patient supply line length, to account for expected $^{82}$Rb decay (and thus loss of activity) in the patient supply line 40 between the positron detector 20 and the patient outlet 10. This arrangement is advantageous in that it allows a user to specify an amount of activity (either activity concentration or total dose) delivered to the patient, and the control loop 42 will operate to match this specification, taking into account the $^{82}$Rb decay within the system 14.

Figure 7A:
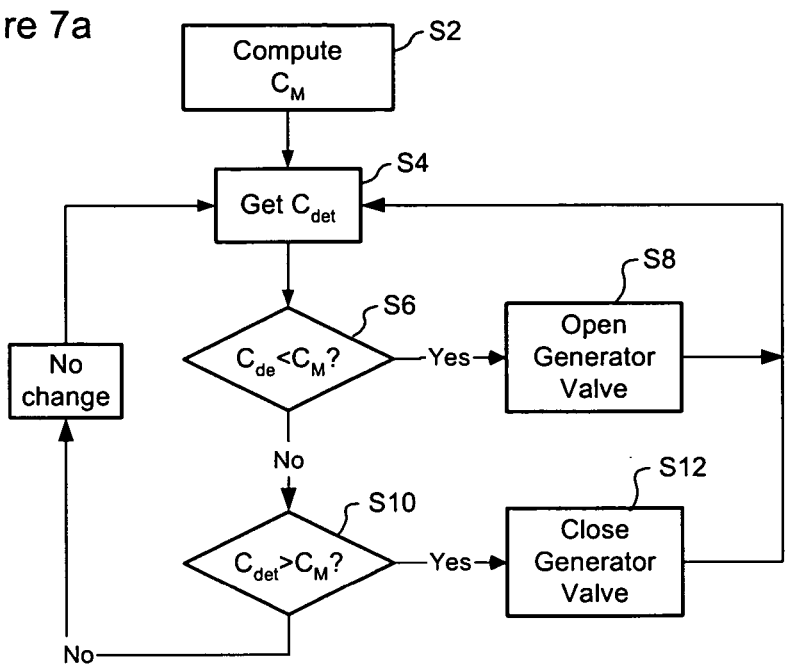
FIGS. 7a-7c schematically illustrate a first algorithm for controlling the Rubidium elution system of FIG. 3.
Figure 7B:
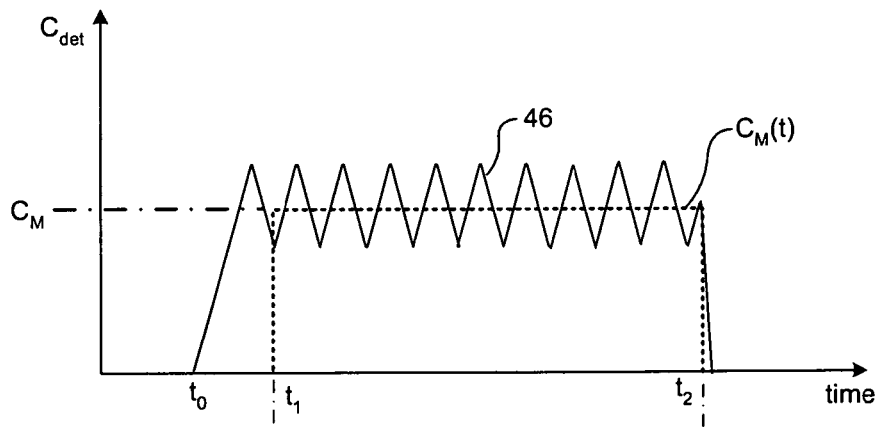

FIG. 7a is a flow chart illustrating a representative threshold-based valve control algorithm which may be used in the embodiment of FIG. 7. For ease of illustration, the flow-chart of FIG. 7a only illustrates the control loop. Process steps and threshold, related to transitioning between various modes of operation are not shown.

In preparation for an elution run, a user enters target parameters for the elution. These parameters may include any three of: total activity dose, target activity concentration, elution duration, and saline flow rate. From the entered parameters, the remaining parameter can be calculated, and, if desired, an adjusted target profile $C'_M(t)$ obtained (step S2).

Figure 1A:
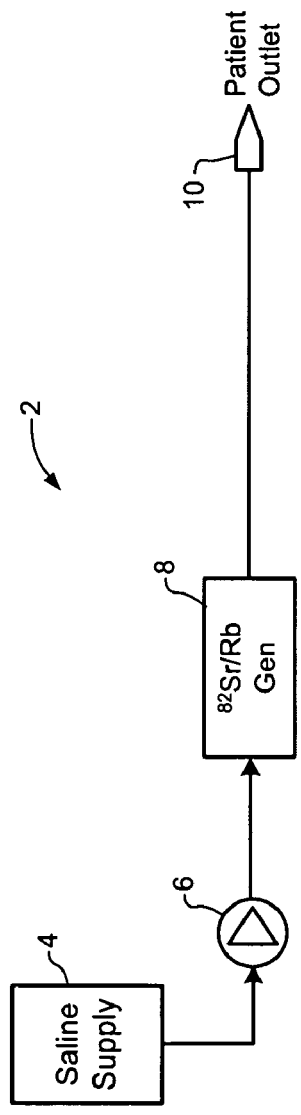
FIG. 1 is a block diagram schematically illustrating principal elements of a conventional Rubidium elution system.
Figure 2B:
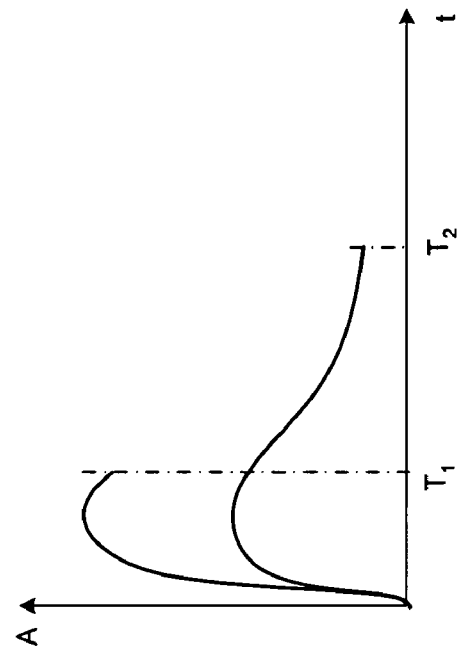
FIGS. 2a and 2b are graphs illustrating representative performance of the elution system of FIG. 1.
Figure 2A:
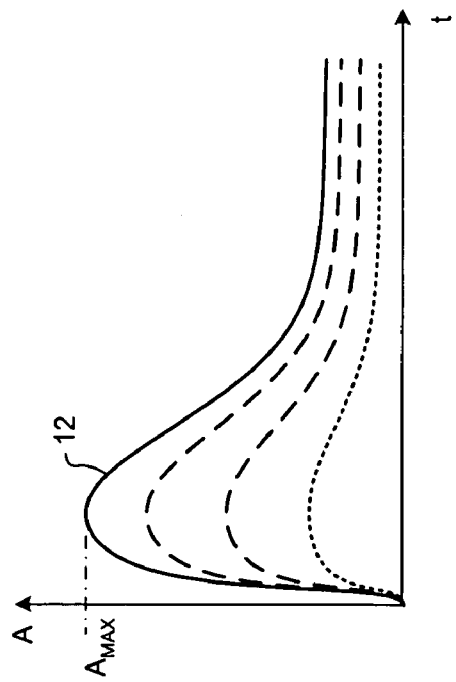

At the start of the elution run, the controller 28 opens the generator valve 16 (at time $t_0$ in FIG. 7b) to place the elution system 14 into the "Waiting for Threshold" mode. During this period, the activity level detected by the positron detector will begin to ramp up following the leading edge of the 'natural' bolus curve 12 (FIG. 2a). During this period, the patient valve 24 remains closed, so that any activity eluted from the generator 8 is passed to the waste reservoir 26. When the detected activity concentration $C_{det}$ exceeds the target value $C_M$, the controller 28 opens the patient valve 24 (at time $t_1$ in FIG. 7b), and shifts to the "elution" mode of operation.

During the elution mode, the controller 28 iteratively obtains an updated concentration parameter $C_{det}$ (at S4), which indicates the instantaneous activity concentration at the positron detector. The concentration parameter $C_{det}$ is then compared to the desired concentration $C_M$. If $C_{det}$ is below the desired concentration $C_M$ (at S6), the generator valve 16 is opened (at S8) so that saline flows through the generator 8 to elute $^{82}$Rb activity. If $C_{det}$ is above the desired concentration $C_M$ (at S10), the generator valve 16 is closed (at S12) so that saline flows through the bypass line 18. As may be seen in FIG. 7b, due to delay in response, the result of this operation is a saw-tooth activity concentration profile 46 centered on the target concentration $C_M$ (or $C'_M$). At the end of the elution run (time $t_2$ in FIG. 7b), the controller 28 closes the generator valve 16 and places the elution system 14 into the "Patient line Flush" mode, which terminates elution of $^{82}$Rb activity from the generator 8 and flushes any remaining $^{82}$Rb activity within the patient line 40 into the patient.

Figure 7C:
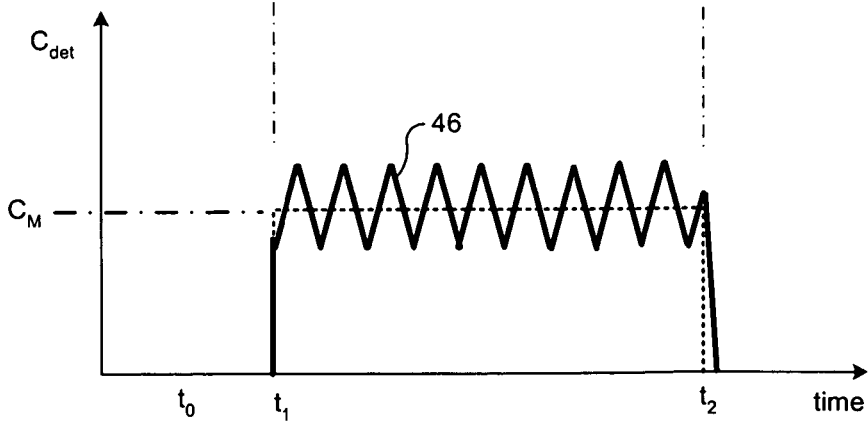

FIG. 7c illustrates the activity concentration profile delivered to the patient as a result of the above-described process. As may be seen from FIG. 7c, no $^{82}$Rb activity is delivered to the patient during the "Waiting for Threshold" mode ($t_0$-$t_1$). During the "elution" mode ($t_1$-$t_2$), the activity concentration 46 follows a saw-tooth pattern centered on the target concentration $C_M$ (or $C'_M$). Finally, in "Patient line Flush" mode (following $t_2$) the activity concentration drops rapidly as $^{82}$Rb elution is terminated and residual activity is flushed from the patient supply line 40.

As will be appreciated, the accuracy with which the delivered activity concentration follows the target profile $C_M(t)$ is largely dependent on the line volume between the merge point 22 and the positron detector 20. In some cases relatively large excursions from the target profile $C_M(t)$ are acceptable. However the control loop response is such that the difference cannot be reduced past a certain limit. As a result, the "error" between the target profile $C_M(t)$ and the delivered concentration profile 46 (FIG. 7c) cannot be eliminated in the embodiment of FIG. 7. A pulse-width modulation technique which overcomes this limitation is described below with reference to FIG. 8.

The embodiment of FIG. 8 differs from that of FIG. 7 primarily in the manner in which the generator valve 16 is controlled. In the embodiment of FIG. 7, the generator valve 16 is opened or closed based on a comparison between the detected activity concentration $C_{det}$ and desired activity concentration. By contrast, in the embodiment of FIG. 8, the generator valve is opened and closed continuously at a predetermined frequency. Any desired frequency may be used, depending primarily on the physical properties of the generator valve 16. In some embodiments, a frequency of between 1 and 10 Hz (e.g. 5 Hz) may be used. In order to control the proportioning of saline flow between the generator 8 and the bypass line 18, the duty cycle of the valve 16 is varied. Thus, for example, a duty cycle of "0" may have the effect of directing the entire saline flow through the bypass line 18, and a duty cycle of "100" directs the entire saline flow through the generator 8. A duty cycle between these limits divides the saline flow between the generator 8 and bypass line 18 in accordance with the duty cycle value. The precision with which the saline flow can be divided between the generator 8 and bypass line 18 will be determined by a minimum adjustment step size, which can be a programmable value.

As described above, the amount of $^{82}$Rb eluted from the generator 8, for any given flow rate, will depend on the recent usage history of the elution system 14, and the instantaneous production rate of $^{82}$Rb within the generator 8. Accordingly, it is possible to improve the accuracy of the elution system 14 by implementing a predictive control algorithm, in which models of the valve 16 and generator performance are used to predict the amount of $^{82}$Rb activity that will be eluted from the generator 8 for a given duty cycle setting.

In particular, the generator performance can be modeled to predict the amount of $^{82}$Rb activity that will be eluted from the generator for a given flow rate, as will be described in greater detail below. In some embodiments, a dose calibrator (not shown) is used to measure the generator performance in terms of, for example, $^{82}$Rb activity concentration vs. eluted volume. This data can be used to predict eluted $^{82}$Rb activity concentration for any given saline flow rate.

In addition, the generator valve response can be modeled to enable a prediction of the flow rate through the generator for any given total saline flow rate (as determined by the pump control setting) and valve duty cycle. In some embodiments, the valve response may be modeled in terms of respective parameters defining upper and lower duty cycle limits $\Pi_{max}$ and $\Pi_{min}$, and a flow ratio vs. duty cycle slope L between the upper and lower limits. With this arrangement, the upper duty cycle limit $\Pi_{max}$ represents the value beyond which all of the flow is considered to be directed into the generator 8. Conversely, the lower duty cycle limit $\Pi_{min}$ represents the value below which all of the flow is considered to be directed into the bypass line 18. The flow ratio vs. duty cycle slope L defines the change in the ratio between the respective flows through the generator 8 and the bypass line 18 for duty cycle values lying between the upper and lower limits.

In cases where the valve response is non linear, it may be advantageous to replace the flow ratio vs. duty cycle slope parameter L with one or more parameters defining a mathematical valve response curve.

At the start of the elution run, the controller 28 opens the generator valve 16 (at time $t_0$ in FIG. 8b) to place the elution system into the "Waiting for Threshold" mode. During this period, the activity level detected by the positron detector 20 will begin to ramp up following the leading edge of the 'natural' bolus curve 12 (FIG. 2a). During this period, the patient valve 24 remains closed, so that any activity eluted from the generator is passed to the waste reservoir 26. When the detected activity concentration reaches the target concentration $C_M$ (or adjusted target $C'_M$, as applicable), the controller 28 opens the patient valve 24 (at time $t_1$ in FIG. 8b), and shifts to the "elution" mode of operation.

During the elution mode, the controller 28 implements a predictive control algorithm in which previously stored generator performance data is used (at S14) to estimate a flow ratio that will yield the target activity concentration $C_M$ (or $C'_M$) at the positron detector 20, for the selected flow rate of the elution run. This estimated (predicted) flow ratio is then used to control the duty cycle of the generator valve 16. The controller 28 then obtains an updated concentration parameter $C_{det}$ (at S16), which indicates the instantaneous activity concentration at the positron detector 20. The concentration parameter $C_{det}$ is then compared to the target concentration $C_M$ (or $C'_M$) to obtain an error function $\Delta C$ (at S18). Based on the value of the error function $\Delta C$, the duty cycle of the generator valve 16 is adjusted. If $\Delta C<0$ (step S20), the duty cycle is increased (at S22) so that proportionally more saline flows through the generator 8 to elute more $^{82}$Rb activity. If $\Delta C>0$ (step S24), the duty cycle is decreased (at S26) so that proportionally more saline flows through the bypass line 18. If neither condition is satisfied the duty cycle is maintained at its current status (S28). As may be seen in FIG. 8b, the result of this operation is a low-error concentration profile 48 that closely matches the target concentration $C_M$ (or $C'_M$). At the end of the elution run (time $t_2$ in FIG. 8b), the controller 28 closes the generator valve 16 (that is, reduces the duty cycle to "0") and places the elution system 14 into the "Patient line Flush" mode, which terminates elution of $^{82}$Rb activity from the generator 8 and flushes any remaining $^{82}$Rb activity within the patient line 40 into the patient.

Figure 8A:
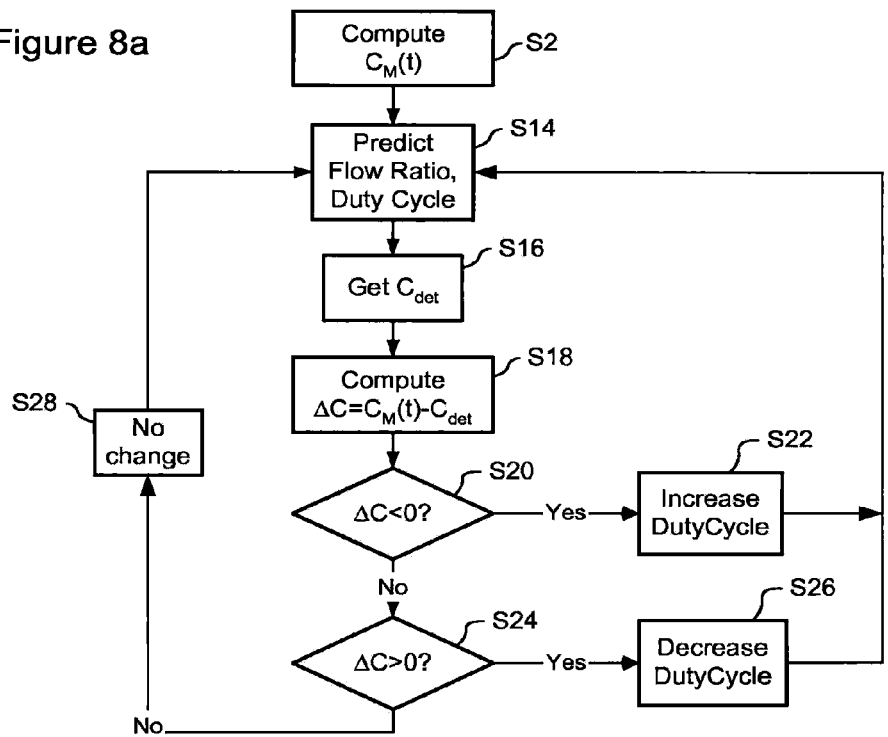
FIGS. 8a-8c schematically illustrate a second algorithm for controlling the Rubidium elution system of FIG. 3.
Figure 8B:
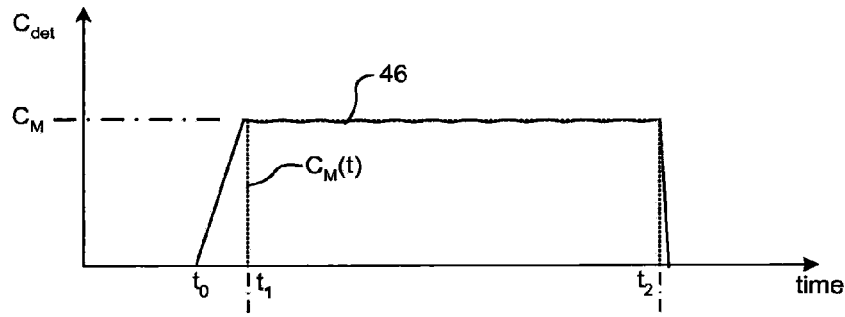
Figure 8C:
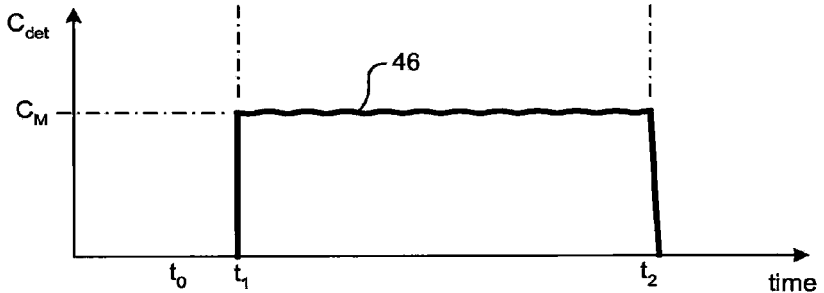

FIG. 8c illustrates the activity concentration profile 48 delivered to the patient as a result of the above-described process. As may be seen from FIG. 8c, no $^{82}$Rb activity is delivered to the patient during the "Waiting for Threshold" mode ($t_0$-$t_1$). During the "elution" mode ($t_1$-$t_2$), the activity concentration closely follows the target concentration $C_M$ (or $C'_M$). Finally, in "Patient line Flush" mode (following $t_2$) the activity concentration drops rapidly as $^{82}$Rb elution is terminated and residual activity is flushed from the patient supply line 40.

In practice, the above-described predictive control algorithm has been found to produce an $^{82}$Rb activity concentration that closely matches the desired target profile $C_M(t)$, except during the first few seconds of the elution, where significant prediction errors may occur. In cases where all of the activity from the generator must be eluted to reach the requested total dosage, this error must be tolerated. However, in other cases it is possible to eliminate the error by delaying the start of the "elution" mode of operation. Thus, for example, during the "waiting for threshold", mode, the detected activity level $C_{det}$ can be monitored and compared to a threshold (e.g. 90% of the target concentration $C_M$). When the threshold level is reached, the generator valve control loop 42 begins operating as described above with reference to FIGS. 8a and 8b, but the patient valve 24 remains closed so that active solution continues to be routed to the waste reservoir 26. After a predetermined delay, the patient valve 24 opens to begin supplying active saline solution to the patient outlet 10. The duration of the delay may be calculated based on the relative activity of the elution. For example, in elutions in which the target activity concentration $C_M$ is less than 10% of the maximum concentration that the generator 8 can produce, a delay of about 10 seconds may be used. Conversely, for elutions in which the target activity concentration $C_M$ is more than about 70% of the maximum concentration that the generator 8 can produce, no delay may be required. For elutions in which the target activity concentration lies between these two limits, an intermediate delay may be calculated.

As described above, the predictive control algorithm uses stored generator performance data to model the generator performance and thereby enable prediction of a valve flow ratio (or, equivalently duty cycle) that will yield the target activity concentration $C_M$ (or $C'_M$) at the positron detector 20. One way of obtaining the generator performance data is to calibrate the elution system 14 by performing a predefined elution run with the patient outlet 10 connected to a conventional dose calibrator (e.g. a Capintec CRC-15). Such a calibration elution run enables the dose calibrator to be used to measure the generator performance in terms of, for example, $^{82}$Rb activity concentration vs. eluted volume. This data can be used to predict eluted $^{82}$Rb activity concentration, for any given saline flow rate, with an accuracy that that will gradually decline with time elapsed since the calibration run. Repeating the calibration run at regular intervals (e.g. once per day) allows the generator performance data to be updated to track changes in the generator performance as the generator 8 ages, and thereby enable accurate flow ratio prediction between successive calibration runs. If desired, calibration elutions can be scheduled to run automatically, for example as part of a daily protocol, which ensures system accuracy and at the same time limiting the potential for human error.

Preferably, calibration elution runs are performed at the same flow rate (e.g. 15 ml/min), and over the same duration (e.g. 1 minute). This enables the known half-life of the $^{82}$Rb (76 seconds) to be used to predict the decay time of activity detected by the dose calibrator. A difference between the predicted and actual decay times indicates breakthrough of $^{82}$Sr. Accordingly, $^{82}$Sr breakthrough can be automatically detected as part of a scheduled system calibration protocol, by sampling the activity level in the dose calibrator at regular intervals throughout the duration of each calibration elution run, and for a predetermined period following completion of the calibration run. The resulting calibration data tracks the activity level within the dose calibrator, as both a function of time and active saline solution volume. Calibration data collected during the elution enables prediction of the $^{82}$Rb decay curve after the elution has stopped. Comparison between this predicted decay curve and the calibration data collected after the elution enables detection of $^{82}$Sr breakthrough.

The calibration data collected during the elution can also be used to calculate the proportionality constant K between the activity parameter $C_{det}$ and the $^{82}$Rb activity concentration. In particular, the instantaneous activity detected by the dose calibrator during the calibration elution is the convolution of the activity concentration and the well known $^{82}$Rb decay curve. Since the saline volumetric flow rate is known, the calibration data collected during the elution can be used to calculate the actual activity concentration of the active saline solution entering the dose calibrator, and thus the proportionality constant K.

In the foregoing description, the predictive control algorithm uses stored generator performance data to predict a valve duty cycle that will yield the target activity concentration $C_M$ (or $C'_M$) at the positron detector, and this estimate is used to control the generator valve 16. An error $\Delta C$ between the detected concentration parameter $C_{det}$ the target activity concentration $C_M$ is then calculated and used to adjust the flow ratio (duty cycle) of the generator valve 16. This error may also be used as data input for a self-tuning algorithm for updating the generator valve response parameters. This functionality is useful for ensuring accuracy of the predictive control algorithm, as well as compensating valve performance changes due, for example, to component aging and wear.

In some embodiments, the self-tuning algorithm uses error data accumulated over a number of elution runs. Thus, for example, during each elution run, desired flow ratios can be calculated (e.g. based on the saline flow rate, target activity concentration $C_M$ and stored generator performance data) and error function $\Delta C$ values stored as a function of desired flow ratio. Accumulation of error value vs. flow ratio data over a number of elution runs can then be processed to obtain a slope error $\Delta L$. This error value can then be used to incrementally adjust the flow ratio vs. duty cycle slope parameter L of the value so as to drive the slope error $\Delta L$ toward zero.

The upper duty cycle limit $\Pi_{max}$ may be adjusted based on error data accumulated during elutions in which the predicted activity concentration from the generator cannot satisfy the desired target value $C_M$. This situation can occur during elution runs conducted toward the end of the useful life of the generator 8, when the $^{82}$Rb production rates are at their lowest. When the predicted activity concentration from the generator 8 is less than the desired target value $C_M$, the predictive control algorithm will operate to set the duty cycle at its upper limit value $\Pi_{max}$. In this condition, if the measured concentration parameter $C_{det}$ is less than the target value $C_M$, the error function value $\Delta C$ will be a non-zero value, and the corrective loop (FIG. 8*a*) will attempt to further increase the duty cycle. If no further increase in the concentration parameter $C_{det}$ occurs (as indicated by a change in the function value $\Delta C$), then the upper limit value $\Pi_{max}$ may be reduced by a predetermined step size (e.g. $10^{-5}$). On the other hand, if operation of the corrective loop does produce an increase in the detected concentration $C_{det}$, the slope of the error data can be used to increase the upper limit value $\Pi_{max}$.

If desired, a similar approach can be used to correct for hysteresis of the valve 16. Hysteresis refers to a system behaving differently depending on the direction of change of an input parameter, usually involving a delayed response. In the case of a bi-state pinch valve of the type illustrated in FIG. 4 the opening and closing latencies may differ. This valve hysteresis manifests itself in the threshold-based elution control algorithm described above with reference to FIG. 7, and appears as a difference between a predicted elution duration (required to achieve a desired eluted activity dose) and the actual elution duration required to obtain that dose. Accordingly, by monitoring the actual elution time for "total activity dose"-type elution runs, it is possible to calculate a hysteresis factor H, which can be applied to the threshold set point (i.e. the target activity concentration $C_M$) to compensate the valve hysteresis.

In the foregoing embodiments, the generator valve is controlled as a bi-state valve, which is either "on" to direct all of the saline solution flow into the generator 8; or "off" to direct all of the saline solution flow into the bypass line 18. In the embodiment of FIG. 7, the generator valve 16 is controlled in precisely this manner, in response to a threshold comparison. In the embodiment of FIG. 8, the valve 16 is cycled continuously at a predetermined frequency (e.g. 5 Hz) and the duty cycle adjusted to emulate a continuously (or step-wise) variable proportioning valve. Both of these methods of valve control are particularly suited to embodiments in which the valve of FIG. 4, for example, is controlled by a solenoid and a spring. However, it will be appreciated that a continuously variable valve could be used, if desired. For example, the position of the valve of FIG. 4 could be controlled by a servo-motor, in which case accurate proportioning of saline flow between the generator and bypass lines could be obtained without cycling the valve between "on" and "off" states. Clearly, use of different generator valve control techniques would imply corresponding differences in the valve control signal and response parameters. However, based on the teachings provided herein, it is considered that all such modifications will be well within the purview of those of ordinary skill in the art, and therefore are contemplated within the scope of the present invention.

The embodiment(s) of the invention described above is(are) intended to be exemplary only. The scope of the invention is therefore intended to be limited solely by the scope of the appended claims.

We claim:

1. A method of controlling an $^{82}$Sr/$^{82}$Rb elution system having a generator valve for proportioning a flow of saline solution between an $^{82}$Sr/$^{82}$Rb generator and a bypass line coupled to an outlet of the generator such that saline solution traversing the bypass line will merge with eluted saline solution emerging from the generator to provide an active saline solution, the method comprising steps of: during each elution run: obtaining a plurality of successive concentration parameter values at predetermined intervals, each concentration parameter value being indicative of a respective instantaneous activity concentration of the active saline solution; computing respective error values between each concentration parameter value and a target activity concentration value of the elution run; and accumulating error data based on a plurality of the computed error values; and between successive elution runs, adjusting at least one performance parameter of the elution system based on the accumulated error data wherein adjusting at least one performance parameter of the elution system comprises an adjustment to a model of the generator valve response.

2. A method as claimed in claim 1, wherein the step of adjusting at least one performance parameter of the elution system comprises a step of tuning a performance model of the generator valve.

3. A method as claimed in claim 2, wherein the accumulated error data comprises the computed error values as a function of an estimated flow ratio.

4. A method as claimed in claim 3, wherein the step of tuning a performance model of the generator valve comprises steps of calculating a slope of the error data; and adjusting a response slope parameter of the generator valve model based on the calculated slope of the error data.

5. A method as claimed in claim 2, wherein the error data comprises one or more error values accumulated during a period in which a target activity concentration of an elution exceeds the predicted activity concentration of that elution.

6. A method as claimed in claim 5, wherein the step of tuning a performance model of the generator valve comprises steps of calculating a slope of the error data; and adjusting an upper limit parameter of the generator valve based on the calculated slope of the error data.

7. A method as claimed in claim 6, wherein the step of adjusting the upper limit parameter comprises steps of: if the calculated slope is zero, reducing the upper limit parameter by a predetermined increment; and otherwise, calculating an adjusted upper limit parameter value using the calculated slope.

8. A method as claimed in claim 2, wherein the error data comprises a difference between a predicted elution duration required to achieve a desired total activity dose and an actual elution duration.

9. A method as claimed in claim 8, wherein the step of tuning a performance model of the generator valve comprises a step of adjusting a hysteresis factor H based on the difference between the predicted and actual elution durations.

10. A method as claimed in claim 1, further comprising a step of enforcing a predetermined delay between successive elution runs.

11. A method as claimed in claim 1, further comprising steps of: defining a plurality of operating modes of the elution system; and during each elution run, automatically transitioning between the operating modes, in accordance with user-input parameters of the elution run.

12. A method as claimed in claim 11, wherein the plurality of operating modes comprise: a "Bypass-to-waste" mode in which the entire saline flow is directed through the bypass line and into a waste reservoir; a "patient line flush" mode in which the saline flow is directed through the bypass line and out through a patient outlet; a "waiting for threshold" mode in which the saline flow is directed through the generator, and the active saline solution directed into the waste reservoir; and an "elution" mode in which the saline flow is proportioned between the generator and the bypass line, and the active saline solution directed out through the patient outlet.

13. A method as claimed in claim 11, wherein the user-input parameters comprise: at least one of a desired duration of the elution, and a desired saline flow rate; and at least one of a target activity concentration profile, and a total eluted activity dose.

14. A method as claimed in claim 1, further comprising steps of: defining a set of one or more predetermined elution runs, each having respective set of predetermined parameters; and executing the set of predetermined elution runs in accordance with a predetermined schedule.

15. A method as claimed in claim 14, wherein the predetermined schedule defines a daily protocol.

16. A method as claimed in claim 14, wherein the set of one or more predetermined elution runs comprises a calibration elution for calibrating any one or more of a performance of the generator; a proportionality constant between the concentration parameter value and the instantaneous activity concentration of the active saline solution.

17. A method as claimed in claim 16, wherein the calibrated performance of the generator comprises either one or both of $^{82}$Rb activity concentration vs. eluted volume; and $^{82}$Sr breakthrough.

* * * * *